United States Patent
Richter

[11] Patent Number: 6,042,341
[45] Date of Patent: Mar. 28, 2000

[54] SUCTION NOZZLE OPERATED WITH COMPRESSED AIR

[76] Inventor: Siegfried Richter, Himmelreich 9, D-88605 Sauldorf-Rast, Germany

[21] Appl. No.: 09/089,026

[22] Filed: Jun. 2, 1998

[30] Foreign Application Priority Data

Nov. 11, 1997 [DE] Germany ............... 297 19 975 U

[51] Int. Cl.[7] ................................................. F04F 5/00
[52] U.S. Cl. .......................... 417/151; 417/77; 417/198; 417/409; 417/500; 15/409; 604/283; 210/130
[58] Field of Search .......................... 376/372; 417/77, 417/151, 198, 500; 210/130; 604/283; 15/409

[56] References Cited

U.S. PATENT DOCUMENTS

| | | | |
|---|---|---|---|
| 3,625,820 | 12/1971 | Gluntz et al. .............. | 376/372 |
| 4,685,870 | 8/1987 | Kato ......................... | 417/500 |
| 4,723,890 | 2/1988 | Corteville et al. ........ | 417/151 |
| 4,792,284 | 12/1988 | Straub et al. ............. | 417/77 |
| 4,892,463 | 1/1990 | Meyer et al. ............. | 417/151 |
| 4,898,517 | 2/1990 | Eriksen .................... | 417/151 |
| 5,167,046 | 12/1992 | Benson ..................... | 15/409 |
| 5,306,265 | 4/1994 | Ragazzi .................... | 604/283 |
| 5,611,673 | 3/1997 | Agata ....................... | 417/198 |
| 5,904,841 | 5/1999 | Penny ....................... | 210/130 |

Primary Examiner—Teresa Walberg
Assistant Examiner—Leonid Fastovsky
Attorney, Agent, or Firm—McGlew and Tuttle, P.C.

[57] ABSTRACT

A suction nozzle operated with compressed air is used to generate vacuum in hollow spaces connected on the suction side. Two cylindrical nozzle bores (1, 2) that are coaxial to one another, through which a compressed air flow flows, which are separated by a suction slit (3) are provided. The nozzle bore (2) on the downstream side has a diameter that is at least slightly larger than the nozzle bore (1) on the upstream side. In order to improve the suction action in the suction slit (3) and to simplify the manufacture, it is provided that a downstream bore (17), which continuously expands in the direction of flow (arrow 4) and whose axial length (a3) corresponds to at least twice the length (a2) of the nozzle bore (2) on the downstream side, is connected to the nozzle bore (2) on the downstream side. The downstream bore (17) has a conical design and has a cone angle (α) of about 3° to 6°.

20 Claims, 7 Drawing Sheets

SUCTION NOZZLE OPERATED WITH COMPRESSED AIR

FIELD OF THE INVENTION

The present invention concerns a suction nozzle operated with compressed air for generating a vacuum in hollow spaces which are connected on the suction side, comprising two cylindrical nozzle bores, which are coaxial to one another and through which the compressed air flow flows, and which are separated from one another by a suction slit, and of which the nozzle bore on the downstream side has a diameter that is at least 1.2 times larger than the nozzle bore on the upstream side.

BACKGROUND OF THE INVENTION

The operating mode of such suction nozzles is based on the Venturi nozzle principle. Such suction nozzles are used in a variety of ways, especially also in the area of medical technology, e.g., for generating a vacuum in the suction electrodes that are to be attached to the human body. Moreover, such suction nozzles are used for suctioning body fluids. In this case, they are connected, on the suction side, to one or more collecting tanks that are in turn connected to a drainage line.

If such suction nozzles are operated by compressed air pumps, then it is especially important that they have a highest efficiency possible, so that even compressed air pumps that operate with relatively low power and therefore with low noise generation may be used.

This means that it must be possible to achieve the greatest suction action possible with the compressed air flow generated by the compressed air pump for generating the greatest vacuum possible in the suction hollow space or spaces of one or more suction electrodes or of one or more collecting tanks of a drainage system.

Also required are a compact design that saves as much space as possible as well as a universal usability and easy handling of such suction nozzles.

SUMMARY AND OBJECTS OF THE INVENTION

The primary object of the present invention is to improve the efficiency of a suction nozzle of the type mentioned in the introduction with simple means, as well as to simplify its manufacture and handling.

This object is accomplished according to the present invention in that a downstream bore that expands continuously in the direction of flow, whose axial length corresponds at least to twice the length of the nozzle bore on the down-stream side, is connected to the nozzle bore on the downstream side.

Vacuum values, which can make up to 80% of the flow pressure of the compressed air, are obtained by means of the solution according to the present invention, whose reproducibility can be proven by a number of tests.

In the prior-art suction nozzles, a cylindrical downstream bore, which is extended in a stepped manner, i.e., by a radial or at least almost radial step to the same diameter over the entire length, which corresponds approximately to twice the diameter of the nozzle bore, is usually connected to the nozzle bores on the downstream side. Only vacuum values that are partly far below 50% of the flow pressure of the compressed air can be obtained with such suction nozzles.

In the tests, it was shown that a certain improvement in the efficiency or in the suction action can already be obtained by means of a plurality of smaller gradations of the diameter within the downstream bore. However, the improvement in the suction action is optimal if the downstream bore is continuously expanded by the diameter of the nozzle bore on the downstream side, i.e., conically, and if the downstream bore has a cone angle between 3° and 6°, but preferably of 4°.

While some of the embodiments of the present invention contribute to optimizing the efficiency, others concern features of the embodiments that make possible a simple manufacture and handling, whereby the advantage is attained that the suction nozzle comprises only two parts which are easy to assemble and are replaceable.

When using the suction nozzle in a medical drainage system the case is provided for in which the nozzle bore on the downstream side is blocked, e.g., by means of contaminants in the compressed air flow and/or the suctioned air. The compressed air flow is then able to escape through the pressure discharge valve, such that the compressed air flow cannot reach a connected collecting tank or the connected drainage tube or tubes.

So that this irregular state of operation of a blocked nozzle bore can be recognized with certainty by the personnel a very simple, cost-favorable and functionally safe sound generator is provided.

In this connection, it is also important that the air that is suctioned from the collecting tank is directed into the environment via a filter, which prevents the discharge of bacteria.

It is guaranteed according to the invention that the compressed air and suction air flowing out of the suction nozzle reaches a place in the environment which it does not disturb and from which it cannot especially be blown into the face of the personnel or of the patient.

The use of the suction nozzle in suction electrodes, which are fixed to the human body by means of vacuum is also provided for. In this case, the filter ring provided is used as a filter for bacteria and sweat, which, moreover, also prevents body hair from being able to reach the suction nozzle.

The invention can also be used to optimize a reliable, airtight fit of the suction electrodes on the human body with an adhesive ring lip.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Referring to the drawings in particular, as can best be seen from FIGS. 4–7, the suction nozzle 70 comprises two cylindrical nozzle bores 1 and 2 that are coaxial to one another, are separated from one another by a narrow suction slit 3, and through which a compressed air flow flows in the direction of the arrow 4.

This compressed air flow is fed through a compressed air line 5, which may be a pipe or a tube, in the direction of the arrow 4. The compressed air line 5 is arranged coaxially to the common system axis 6, and it ends directly in front of or at the face of a sleeve body 8, in which the nozzle bore 1 on the upstream side is placed.

The nozzle bore 1 on the upstream side is located in a front wall 9 of the sleeve body 8, to which a stepped cylindrical projection 10 of the sleeve body 8 is connected.

In this cylindrical projection 10, a flow funnel 11, which tapers in the direction of flow (the arrow 4) to the cross section of the nozzle bore 1 on the upstream side, is located directly in front of the nozzle bore 1 on the upstream side.

Figure 4:
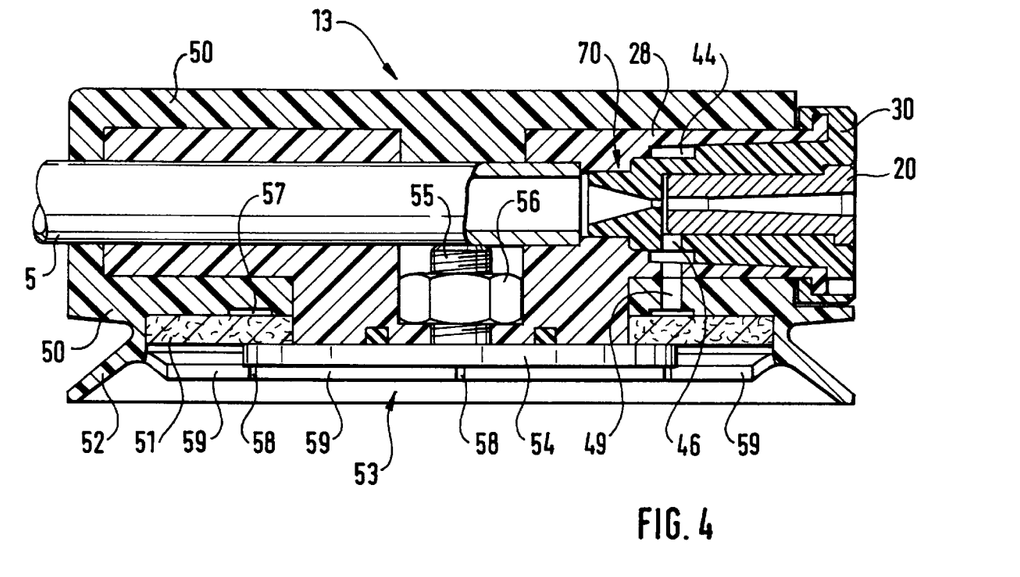
FIG. 4 is an enlarged view of section IV—IV from FIG. 2.
Figure 5:
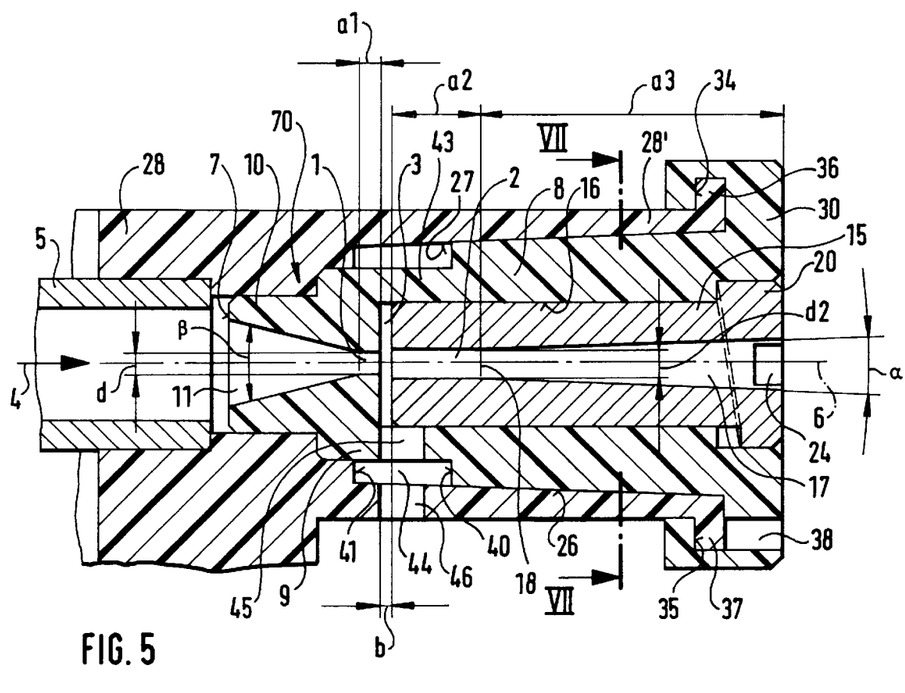
FIG. 5 is an enlarged sectional view of the complete suction nozzle, as it is installed in the suction electrode.
Figure 6:
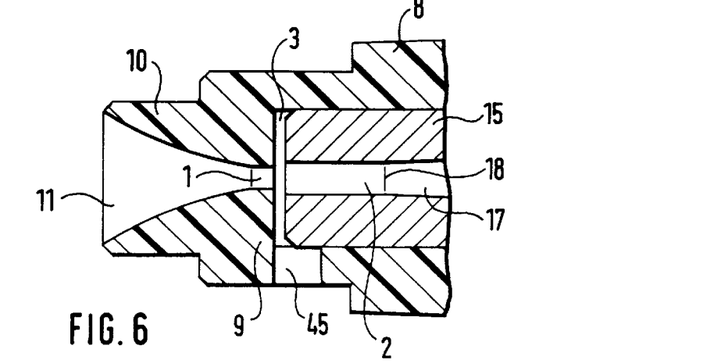
FIG. 6 is a sectional view of a section of the suction nozzle in a changed embodiment.
Figures 8, 9, 10:
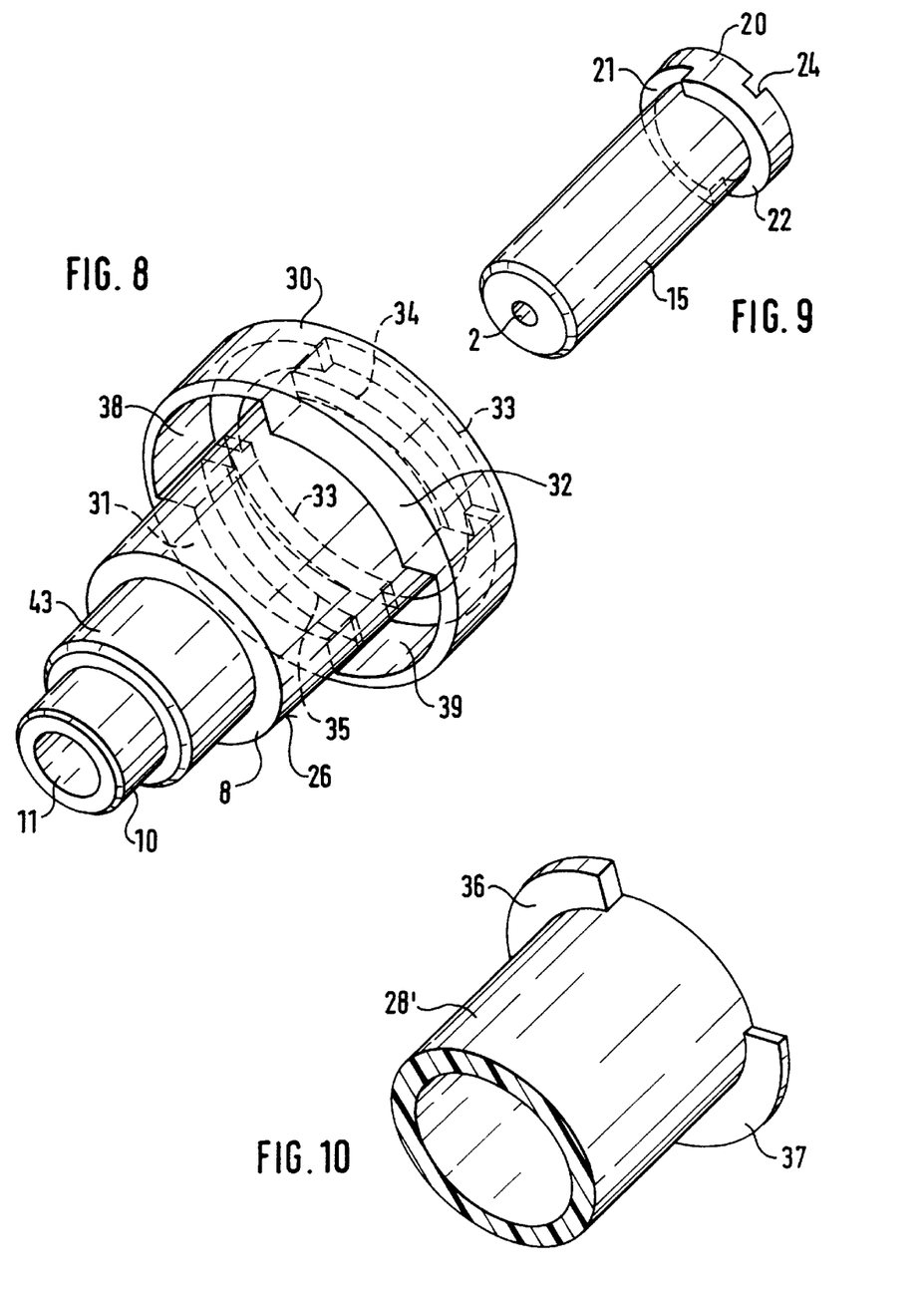
FIG. 8 is a perspective side view of the sleeve body of the suction nozzle.
FIG. 9 is a perspective side view of the nozzle body of the suction nozzle.
FIG. 10 is a perspective view of a part of the housing body that receives the suction nozzle.
Figure 11:
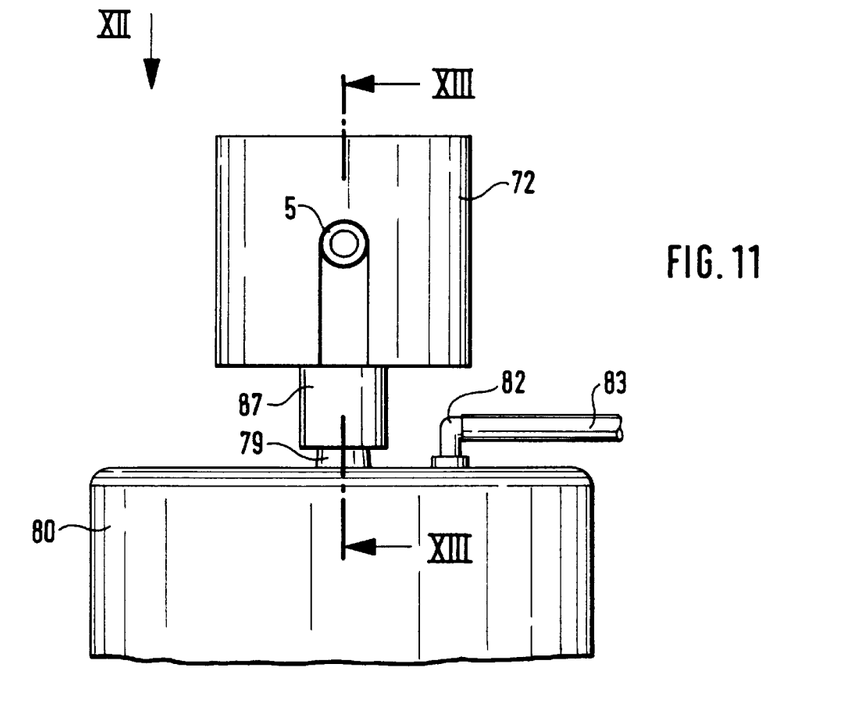
FIG. 11 is a suction nozzle head placed on a collecting tank.
Figure 12:
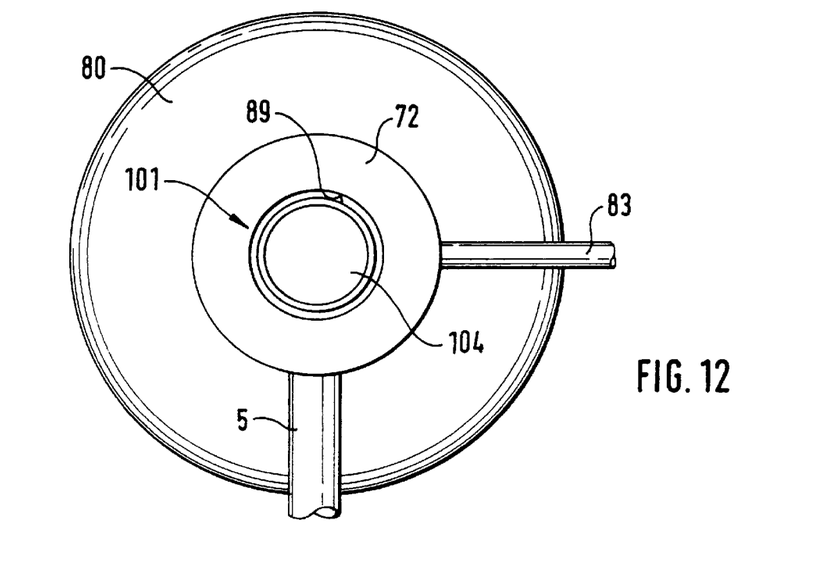
FIG. 12 is a top view XII from FIG. 11.

In the embodiment of FIGS. 4, 5 and 8, this flow funnel 11 has a conical shape. However, its influence on the efficiency of the suction nozzle 70 may be improved in that its shape, as shown in FIG. 6, has a trumpet-like design.

The cone angle β of the flow funnel 11 shall advantageously be between 25° and 35°, whereby the opening diameter of the flow funnel 11 on the upstream side should be at least almost matched with the internal diameter of the compressed air line.

It is also important that the axial length a1 of the nozzle bore 1 on the upstream side be at least as great as its diameter d.

The nozzle bore 2 on the downstream side that is separated from the nozzle bore 1 on the upstream side by the suction slit 3 is located in a cylindrical nozzle body, which is inserted airtightly into a cylindrical hollow space 16 of the sleeve body 8.

A continuously expanding downstream bore 17 that has a conical shape with a cone angle α that may be 3° to 6°, but preferably 4°, is connected directly to the nozzle bore 2. Thus, it is also important that the passage 18 between the cylindrical nozzle bore 2 and the downstream bore 17 have a rounded rather than sharp-edged design.

While the axial length a2 of the nozzle bore 2 on the downstream side is at least twice as great as the length a1 of the nozzle bore 1 on the upstream side, the diameter d2 of the nozzle bore 2 is about 1.2 times greater than the diameter d of the nozzle bore 1 on the upstream side.

The axial length a3 of the downstream bore 17 is important for achieving a high efficiency of the suction nozzle as well. This length a3 shall be at least twice as great as the length a2 of the nozzle bore 2, to which the downstream nozzle 17 is connected. However, it is more advantageous if the axial length a3 of the downstream bore 17 corresponds to at least three times the length a2 of the nozzle bore 2 on the downstream side.

In order to be able to adjust the narrow suction slit 3, which is at most as great as the diameter of the smallest nozzle bore 1, to an optimal width b in an exact manner, the nozzle body 15 is provided with an adjusting head 20, which has a greater diameter than the remaining part of the nozzle body 15. This adjusting head 20 is provided with two thread-like supporting surfaces 21 and 22 (cf. FIG. 9), which lie on likewise thread-like opposite surfaces (23) (FIG. 5) of the sleeve body 8.

In order to be able to use a screwdriver, e.g., to adjust the nozzle body 15, its adjusting head 20 is provided with cross slits 24 on the front side. By means of a corresponding axial pressure on the tool placed in the cross slits 24 on the adjusting head and a rotation in one or the other direction, the nozzle body 15 can be adjusted axially in the hollow space 16 of the sleeve body 8 by means of the thread-like supporting surfaces 21 and 22 on the opposite surfaces 23 of the sleeve body 8. Of course, a corresponding snug fit of the cylindrical part of the nozzle body 15 in the cylindrical hollow space 16 of the sleeve body 8 is necessary for this purpose. It is also readily possible, but more expensive, to provide the nozzle body 15 and the cylindrical hollow space 16 each with a threaded section.

By means of this thus designed adjusting head 20, the width b (FIG. 5) of the suction slit 3 can be adjusted to the optimal value very easily. It is a matter of course that a pressure gauge, which displays the vacuum generated, is additionally connected to a suction line connected to the suction slit 3.

The sleeve body 8 is provided with a peripheral section 26, which tapers conically against the upstream direction (arrow 4), which section 26 is received in a conical receiving bore 27 of a housing body 28 in a fitting manner, i.e., airtightly.

Figure 7:
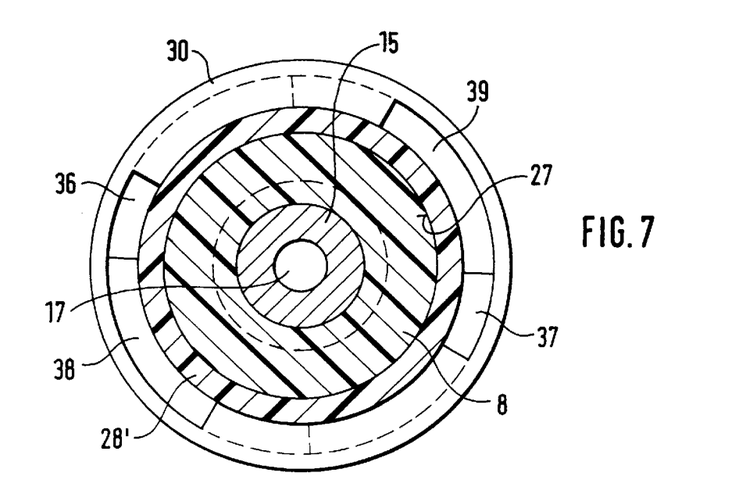
FIG. 7 is a section VII—VII from FIG. 5.

As can best be seen from FIG. 7, the housing body 28 has a cylindrical shoulder 28', in which the conical receiving bore 27 for the sleeve body 8 is arranged coaxially to the axis of the outer jacket surface and thus coaxially to the system axis 6 as well.

To obtain an airtight snug fit between the conical peripheral section 26 and the wall of the receiving bore 27, as well as to be able to fasten this, the sleeve body 8 is provided on the downstream side with a tensioning ring 30 that can be tensioned by means of ring shoulder segments 31 and 32 which have thread-like running supporting surfaces 34 and 35, on flange ring segments 36 and 37. So that these flange ring segments 36 and 37 can be inserted into the tensioning ring on the front side the tensioning ring 30 is provided with ring-segment-like recesses 38 and 39, to which segment-like hollow spaces having the thread-like running supporting surfaces 34 and 35 are connected in the peripheral direction. In the sleeve body 8 made of inherently stable plastic, each of these supporting surfaces 34, 35 lies in the area of two ring-segment-like cutouts 33, which are open on the front side and which are diametrically opposite.

Thus, the sleeve body 8 can easily be fastened like a bayonet catch in the housing body 28 and can also again be easily removed from this body. This means that the sleeve body 8 is arranged easily replaceably with the nozzle body 15 inserted in the housing body 28 or its section 28', which in practice represents a significant advantage.

As is apparent from FIG. 5, the conical receiving bore 27 has a greater axial length than the conical peripheral section 26 of the sleeve body 8. As a result, a ring slit 44 forms between a radial shoulder 40 that is present on the upstream-side end of the conical peripheral section 26 and a ring shoulder 41 at the end of the conical receiving bore 27 lying radially in front of the suction slit 3 around a cylindrical shoulder 43 of the sleeve body 8.

A radial bore 45 of the sleeve body 8, which connects the suction slit 3 to the ring slit 44, opens into this ring slit 44. The ring slit 44 and thus also the suction slit are connected to the outer surroundings via a bore 46 in the wall of the cylindrical shoulder 28' of the housing body 28 that is coaxial to the radial bore 45.

In the exemplary embodiment of FIGS. 1 through 7, in which the suction nozzle 70 is placed in the housing body 28 of a suction electrode 13, the bore 46 is connected via an inserted filter ring 52 to a hollow space 53 surrounded by an elastic adhesive ring lip 52 via a bore 49 of a suction electrode housing 50 surrounding the housing body 28 that is coaxial thereto.

The entire suction electrode housing 50, which surrounds the housing body 28, is made of elastic material. A circular, metallic electrode plate 54 in the hollow space 53 is arranged at the bottom side of the housing body 28 which is made of an inherently stable material, especially plastic, and is fastened by a threaded stem 55, which is screwed into a threaded nut, and at the same time, is connected in an electrically contacting manner to the compressed air line, which is preferably made of metal so that this compressed air line can be connected, e.g., to an electrical monitoring, measuring or recording device via another electrical line.

As is apparent from FIG. 4, the bore 49 opens into an annular groove 57 of the suction electrode housing 50, which annular groove 57 is concentric to the threaded stem, through which the suction action is distributed over the entire periphery of the filter ring 51.

To obtain a good adhesion of the adhesive ring lip 52 when placing the suction electrode 13 on highly curved body surfaces of a patient, a ring-shaped auxiliary lip 52', which is axially set back and tapers conically inwards and is divided into a plurality of ring sectors 59 by a plurality of radial slits 58, is provided with this adhesive ring lip 52 on the inside.

The adhesive ring lip 52 which is made of elastic material and has a thin-walled design has a conical, outward-expanding shape. By the connection to the auxiliary lip 52' described, a pivoting of the adhesive ring lip 52 inwards can be brought about in the areas, in which the auxiliary lip 52' is pressed onto a highly curved part of the patient's body, so that, as a result, it is possible to guarantee an adhesion, on the body surface of the patient, of the adhesive ring lip 52 which seals tightly on the entire ring periphery.

Thus, it is advantageous if, as already mentioned, the auxiliary lip 52' is divided into a plurality of ring sectors 59 by means of a plurality of radial slits 58.

Figure 1:
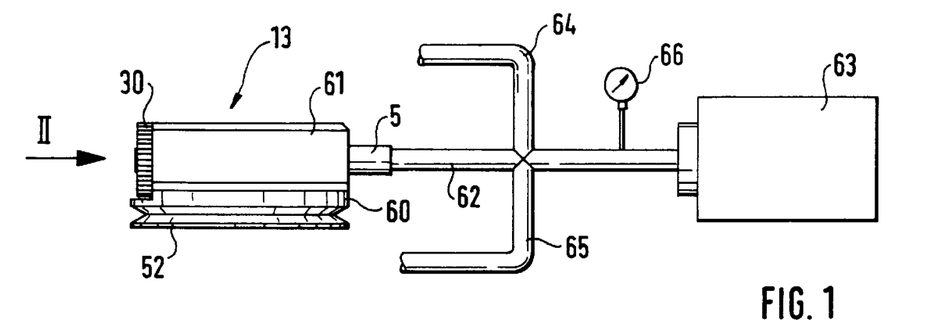
FIG. 1 is a simplified side view of a suction electrode with the suction nozzle installed, which is connected to a compressed air source.
Figure 2:
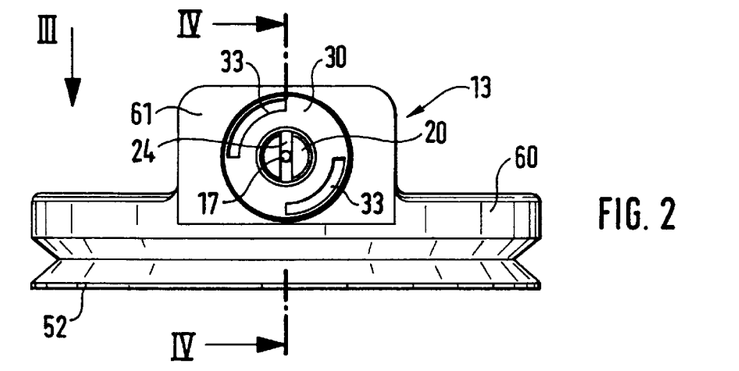
FIG. 2 is an enlarged view of a side view II of the suction electrode of FIG. 1.
Figure 3:
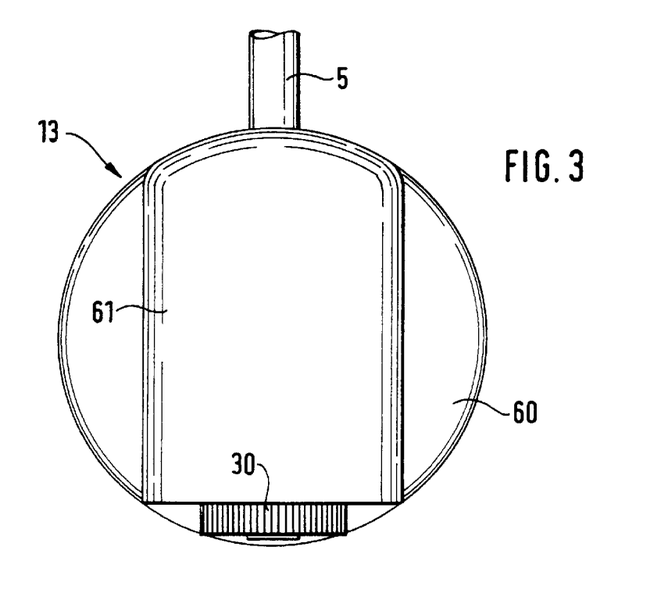
FIG. 3 is the top view III of the suction electrode of FIG. 2.

As is apparent from FIGS. 1 to 3, the suction electrode 13 comprises a circular, plate-shaped bottom part 60, whose bottom side forms the adhesive ring lip 52, and an approximately cuboid top part 61, in which the suction nozzle 70 and the compressed air line 5 are arranged coaxially to one another.

The compressed air line 5 of the suction electrode 13 is connected via a connecting line 62 to a compressed air source 63. The connecting line 62 may be provided with a plurality of branch lines 64 and 65 for the connection of other suction electrodes 13. Moreover, a pressure gauge 66 may also be provided for monitoring the operation.

In the exemplary embodiment shown in FIGS. 11 to 14, the suction nozzle 70 is inserted into the housing body 78 of a suction head 72. This suction head 72 is placed detachably on the conical connecting socket 79 of a collecting tank 80. The collecting tank 80 is provided with a tube connecting socket 82 in its cover wall 81, to which connecting socket 82 a drainage line 83 is connected for suctioning the body fluid of a patient.

In this type of use, the sleeve body 8 is provided with a tube connecting socket 73, which is connected directly to the part, in which the flow funnel 11 is located. Here, the bore 75 of the tube connecting socket 73 has a diameter, which corresponds to the end diameter of the flow funnel 11 on the suction side. The compressed air for operating the suction nozzle 70 in the direction of the arrow 4 is supplied by a compressed air line 5, which is slipped onto the tube connecting socket 73. Besides, the suction nozzle 70 has the same design as in the exemplary embodiment that is described based on FIGS. 4 to 10.

Figure 13:
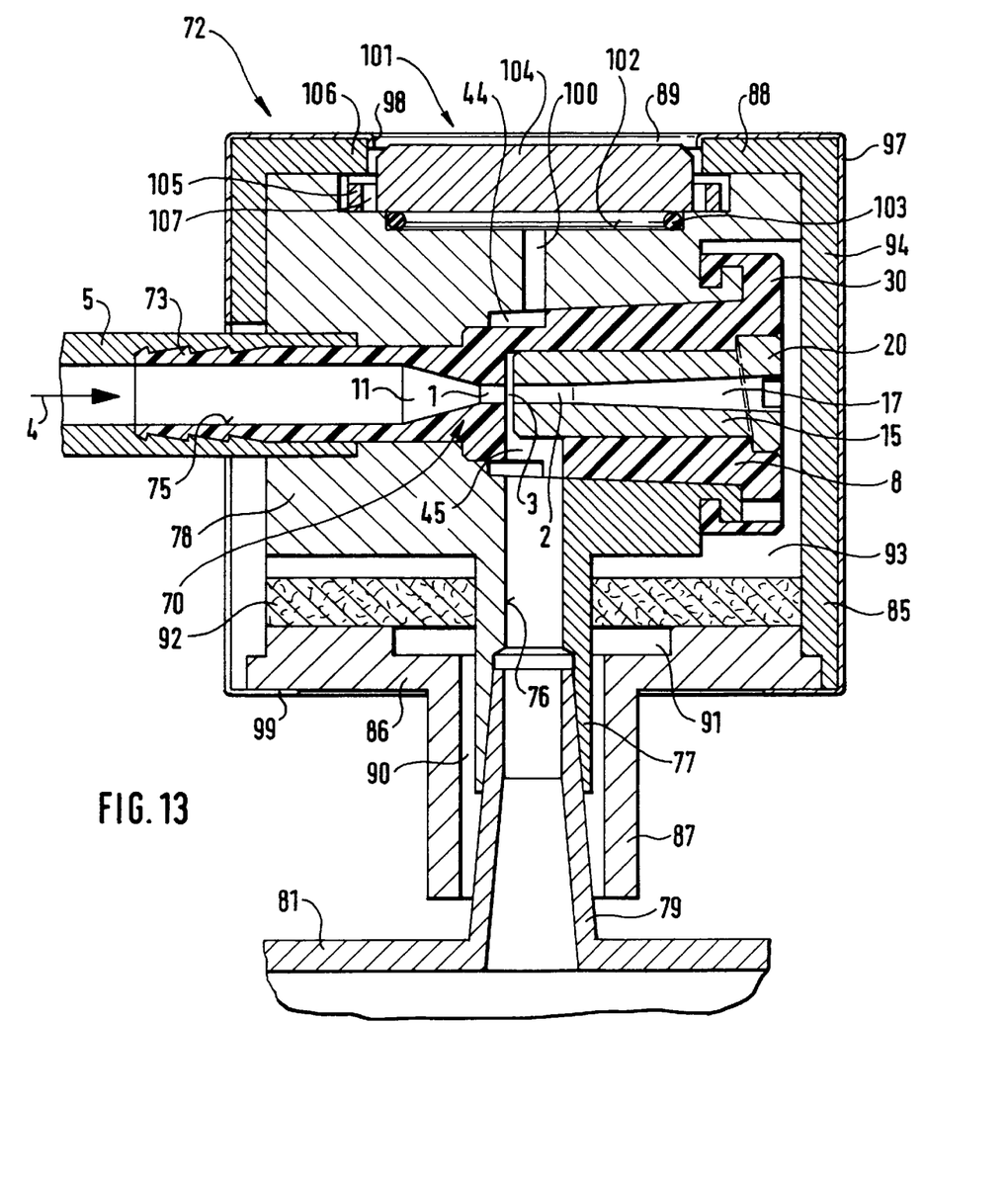
FIG. 13 is an enlarged sectional view of a suction nozzle head according to the sectional line XIII—XIII from FIG. 11.

The radial bore 45 of the sleeve body 8 opens partly into the ring slit 44 and partly into a suction bore 76 of the housing body 78. This suction bore 76 continues in a cylindrical suction pipe socket 77 which is made into an integral element at the bottom side of the housing body 78 and can be placed or is placed in a fitting manner onto the conical connecting socket 79 of the collecting tank 80.

The housing body 78 and suction nozzle 70 arranged therein are surrounded by a protective housing 85, which has an annular wall 94, a bottom wall 86 with an exhaust pipe socket 87 and a cover wall 88 with a central discharge opening 89. The exhaust pipe socket 87 is arranged concentrically to the suction pipe socket 77 and is provided with a cylindrical exhaust opening 90, which surrounds the suction pipe socket 77 in a ring-shaped manner and whose diameter is greater than the outer diameter of the connecting socket 79 of the collecting tank 80 as well. The exhaust pipe socket 77 ends at a certain distance from the top side of the cover wall 81 of the collecting tank 80, so that the exhaust opening 90 is open at the bottom.

On the inside of the bottom wall 86, a cylindrical, ring-shaped expansion 91, which is covered by a plate-shaped filter 92, is arranged connected to the exhaust opening 90. Via this filter 92, this recess 91, or the exhaust opening connected thereto, is connected to a hollow space 93 of the protective housing 85, which hollow space 93 is also present between the cylindrical annular wall 94 of the protective housing 85 and the front side of the suction nozzle 70 on the downstream side or of the sleeve body 8 and of the nozzle body 15. Thus, the exhaust bore 17 opens into this hollow space 93, so that the compressed air flow can reach the environment by means of this hollow space 93 via the filter 92 and the exhaust opening 90 above the cover wall 81 of the collecting tank 80.

To be able to insert the housing body 78 with the inserted suction nozzle 70 and its tube connecting socket 73 from below into the protective housing 85, this protective housing 85 is provided with a slit opening 96 in its annular wall 94 that is open on the bottom side or is subsequently sealed by the stepped bottom wall 86. The protective housing itself is covered with a sleeve-like metal jacket 97, which is provided with a crimped edge 98 in the area of the discharge opening 89 and which also has a crimped edge 99 at the bottom side of the bottom wall 86.

So that the compressed air flowing in cannot reach the drainage line 83 via the collecting tank 80 in the case of a blockage of the nozzle bore 2 on the downstream side of the suction nozzle 70, the ring slit 44 that is connected to the bore 45 of the sleeve body 8 is connected to a pressure discharge valve 101 by means of a vertical bore 100. This pressure discharge valve 101 comprises a sealing ring 103, which lies in a cylindrical recess 102 of the housing body 78, and a valve plate 104 lying loosely on this body 78. This valve plate 104 has a ring flange 105, which grasps the edge 106 of the cylindrical discharge opening 89 of the cover wall 88 from below with radial and vertical clearance. This ring flange 105 may be provided with a plurality of axial bores 107, through which the compressed air, which should not reach the collecting tank 80 if the nozzle bore 2 is blocked, may escape outwards through the discharge opening 89 more quickly.

During normal operation, i.e., if the nozzle bore 2 is not blocked and a vacuum is produced in the ring slit 44, the valve plate 104 of the pressure discharge valve 101 is pressed tightly against the sealing ring 103.

Since the blocking of the nozzle bore 2 cannot easily be recognized due to a lack of external signs, it is advantageous to provide a device that indicates this malfunction to the personnel or to the patient who is connected to the drainage system.

Since a sound generator can easily be excited by an air flow to generate a sound, it is advantageous to provide the pressure discharge valve with a sound generator that always generates an acoustic signal if the compressed air escapes through the pressure discharge valve 101.

For this purpose, it is possible to place, on the discharge opening 89, a sound generator that generates a whistling sound, e.g., with a corresponding air flow through the pressure discharge valve.

Figure 14:
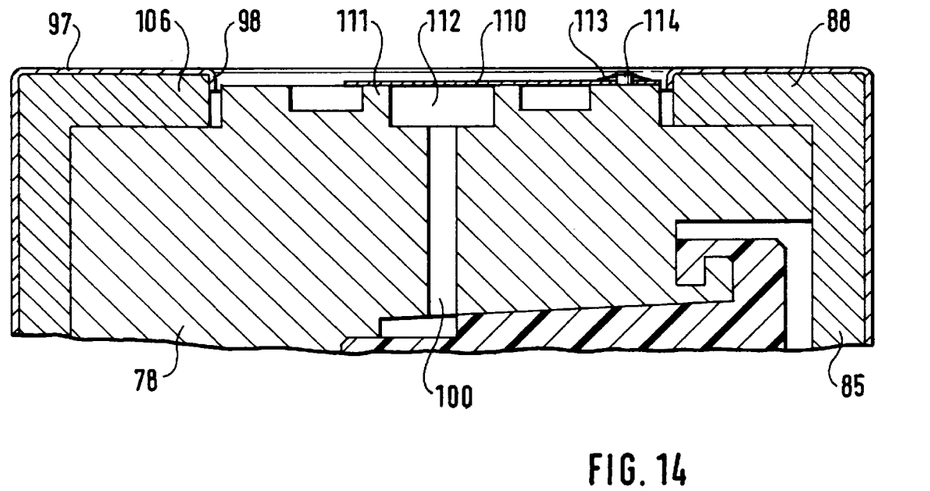
FIG. 14 is a highly enlarged sectional view of another embodiment of the pressure discharge valve.

However, a thin valve tongue 110, which lies on a valve ring rib 111 in a spring-like manner according to FIG. 14, which rib 111 surrounds a cylindrical recess 112 of the housing body 78, into which recess 112 the bore 100 opens, may also be used as a sound generator. Advantageously, this valve tongue 110 has an oblong shape. It is fastened to a vertical stem 114 by means of a spring washer 113. During normal operation, in which a vacuum is produced both in the bore 100 and in the recess 112, the valve tongue 110 is suctioned in a sealing manner. If, however, the compressed air flow lifts the valve tongue 110 off the valve ring rib 111 during a blockage of the nozzle bore 2, a buzzing noise or shrill sound, which can be clearly detected, is generated if the spring system is adjusted correctly.

Thus, the valve tongue of the pressure discharge valve is at the same time used as a sound generator.

Thus, additional safety against harmful operating troubles is also given for this application.

At an available flow pressure of 0.5 to 1 bar, suction nozzles of the type described above with a nozzle bore on the upstream side having a diameter of about 0.3 mm to 0.6 mm have proven their worth.

E.g., a vacuum of −0.65 bar during continuous operation was obtained with a compressed air flow pressure of 0.8 bar.

While specific embodiments of the invention have been shown and described in detail to illustrate the application of the principles of the invention, it will be understood that the invention may be embodied otherwise without departing from such principles.

What is claimed is:

1. A suction nozzle having a suction side and being operated by a flow of compressed air for generating a vacuum in hollow spaces connected on the suction side, the suction nozzle comprising:

a first cylindrical nozzle bore;

a second cylindrical nozzle bore disposed coaxial to said first cylindrical nozzle bore, compressed air flow flowing through said first cylindrical nozzle bore and said second cylindrical nozzle bore;

a suction slit separating said first cylindrical nozzle bore and said second cylindrical nozzle bore from one another, said second nozzle bore being on a downstream side and having a diameter that is at least slightly larger than said first nozzle bore on a first side; and a downstream bore continuously expanding in a direction of flow, said downstream bore having an axial length corresponding at least to twice an axial length of said second cylindrical nozzle bore and being connected to said second cylindrical nozzle bore on a downstream side of said second cylindrical nozzle bore.

2. The suction nozzle in accordance with claim 1, wherein the downstream bore has a conical design and has a cone angle (α) of from 3° to 6°.

3. The suction nozzle in accordance with claim 1, wherein said axial length of said downstream bore corresponds to three times said axial length of said second cylindrical nozzle bore.

4. The suction nozzle in accordance with claim 1, wherein said second cylindrical nozzle bore is downstream of said first cylindrical nozzle bore and a connecting part between said second cylindrical nozzle bore and the said downstream bore is rounded.

5. The suction nozzle in accordance with claim 1, wherein said first cylindrical nozzle bore is upstream of said second cylindrical nozzle bore and said first cylindrical nozzle bore has an axial length that is equal to or greater than a diameter of said first cylindrical nozzle bore.

6. The suction nozzle in accordance with claim 5, wherein said axial length of said second cylindrical nozzle bore is at least twice as great as said axial length of said first cylindrical nozzle bore.

7. The suction nozzle in accordance with claim 1, wherein said first cylindrical nozzle bore is upstream of said second cylindrical nozzle bore and a flow funnel, tapering in the direction of flow to the cross section of said first cylindrical nozzle bore, is arranged upstream of said first cylindrical nozzle bore.

8. The suction nozzle in accordance with claim 7, wherein said flow funnel has a trumpet-like shape.

9. The suction nozzle in accordance with claim 1, further comprising: a nozzle body and a sleeve body that is provided with a front wall and a cylindrical hollow space wherein said first cylindrical nozzle bore is upstream of said second cylindrical nozzle bore and said first cylindrical nozzle bore is arranged in said front wall of said sleeve body coaxially to sleeve body axis, said second cylindrical nozzle bore being arranged with said downstream bore to be connected in said nozzle body installed airtightly in said cylindrical hollow space of said sleeve body.

10. The suction nozzle in accordance with claim 9, wherein said nozzle body can be adjusted axially in said hollow space of said sleeve body by means of thread-like supporting surfaces.

11. The suction nozzle in accordance with claim 9, further comprising a housing body with a conical receiving bore wherein said sleeve body has a peripheral section, which tapers conically against an upstream direction and which is received in a fitting manner in said conical receiving bore of said housing body.

12. The suction nozzle in accordance with claim 11, wherein said sleeve body is provided on a downstream side with a tensioning ring that can be tensioned axially by means of ring shoulder segments with thread-like running supporting surfaces on said flange ring segments of said housing body.

13. The suction nozzle in accordance with claim 9, further comprising a housing body wherein said housing body is provided with a pressure discharge valve, which is connected to a suction bore via a ring channel, which surrounds a part of said sleeve body, and/or via a bore, which suction bore is in turn connected to said suction slit.

14. The suction nozzle in accordance with claim 13, wherein said pressure discharge valve is provided with a sound generator.

15. The suction nozzle in accordance with claim 14, wherein a thin valve tongue, which lies on a valve ring surface tightly under a spring tension, is provided as said sound generator.

16. The suction nozzle in accordance with claim 9, further comprising a housing body wherein said housing body is surrounded by a protective housing that has an exhaust opening, which is connected via a filter to a housing space, into which said downstream bore opens.

17. The suction nozzle in accordance with claim 16, wherein said exhaust opening is located in an exhaust pipe socket, in which said suction pipe socket with said suction bore is arranged.

18. The suction nozzle in accordance with claim 9, further comprising a housing body wherein said housing body as a core part is designed as a suction electrode provided with an adhesive ring lip, in which the space surrounded by said adhesive ring lip is connected via an inserted filter ring to said suction slit.

19. The suction nozzle in accordance with claim 18, wherein said adhesive ring lip, which is made of elastic material and has a thin-walled design, has a conical, outward-expanding shape and is provided on its inside with a circumferential auxiliary lip that is axially set back and tapers conically inwards.

20. The suction nozzle in accordance with claim 19, wherein said auxiliary lip is divided into a plurality of ring sectors by means of radial slits.

* * * * *